United States Patent
Hirai et al.

(10) Patent No.: US 10,143,431 B2
(45) Date of Patent: Dec. 4, 2018

(54) MEDICAL IMAGE PROCESSING APPARATUS AND METHOD, AND RADIOTHERAPEUTIC APPARATUS

(71) Applicants: TOSHIBA ENERGY SYSTEMS & SOLUTIONS CORPORATION, Kawasaki-shi (JP); National Institutes for Quantum and Radiological Science and Technology, Chiba-shi (JP)

(72) Inventors: Ryusuke Hirai, Shinagawa (JP); Yukinobu Sakata, Kawasaki (JP); Yasunori Taguchi, Kawasaki (JP); Fumi Maruyama, Miura (JP); Shinichiro Mori, Chiba (JP)

(73) Assignees: TOSHIBA ENERGY SYSTEMS & SOLUTIONS CORPORATION, Kawasaki-shi (JP); NATIONAL INSTITUTES FOR QUANTUM AND RADIOLOGICAL SCIENCE AND TECHNOLOGY, Chiba-Shi (JP)

( * ) Notice: Subject to any disclaimer, the term of this patent is extended or adjusted under 35 U.S.C. 154(b) by 0 days.

(21) Appl. No.: 15/433,262

(22) Filed: Feb. 15, 2017

(65) Prior Publication Data
US 2017/0231586 A1 Aug. 17, 2017

(30) Foreign Application Priority Data
Feb. 16, 2016 (JP) .................................. 2016-027432

(51) Int. Cl.
A61B 6/00 (2006.01)
A61B 6/02 (2006.01)
(Continued)

(52) U.S. Cl.
CPC .............. *A61B 6/487* (2013.01); *A61B 6/022* (2013.01); *A61B 6/0407* (2013.01);
(Continued)

(58) Field of Classification Search
CPC ........... A61B 6/487; A61B 6/54; A61B 6/022; A61B 6/5223; A61B 6/5288;
(Continued)

(56) References Cited

U.S. PATENT DOCUMENTS

| | | | | |
|---|---|---|---|---|
| 7,158,610 B2* | 1/2007 | Mostafavi | ............ | A61B 6/4441 378/62 |
| 7,260,426 B2* | 8/2007 | Schweikard | ............. | A61B 6/12 600/407 |
| 7,366,336 B2* | 4/2008 | Hristov | ..................... | G06T 7/38 382/131 |
| 7,570,738 B2* | 8/2009 | Khamene | ............... | A61B 6/032 378/20 |

(Continued)

*Primary Examiner* — Brenda C Bernardi
(74) *Attorney, Agent, or Firm* — Oblon, McClelland, Maier & Neustadt, L.L.P.

(57) ABSTRACT

A medical image processing apparatus, includes: a reconstructed moving image obtainer that obtains a reconstructed moving image; a focus region identifier that identifies a first focus region corresponding to the designated focus; a fluoroscopic moving image obtainer that obtains at least one-period data on a fluoroscopic moving image; a second characteristics identifier that identifies each of two or more second characteristics regions corresponding to the internal body portion; a comparison selector that compares the two or more first characteristic regions; a conversion parameter calculation unit that calculates a conversion parameter for converting the first characteristic region.

7 Claims, 7 Drawing Sheets

(51) Int. Cl.
*A61B 6/04* (2006.01)
*A61N 5/10* (2006.01)
*G06T 11/00* (2006.01)

(52) U.S. Cl.
CPC .......... *A61B 6/5223* (2013.01); *A61B 6/5288* (2013.01); *A61B 6/54* (2013.01); *A61N 5/1039* (2013.01); *A61N 5/1049* (2013.01); *A61N 5/1067* (2013.01); *A61N 5/1077* (2013.01); *G06T 11/003* (2013.01); *A61N 2005/1061* (2013.01)

(58) Field of Classification Search
CPC .. A61N 5/1039; A61N 5/1077; A61N 5/1049; A61N 5/1067; A61N 2005/1061; G06T 11/003
See application file for complete search history.

(56) References Cited

U.S. PATENT DOCUMENTS

| | | | |
|---|---|---|---|
| 8,831,706 B2* | 9/2014 | Fu | A61B 6/032 378/65 |
| 9,114,253 B2* | 8/2015 | Dempsey | A61B 5/055 |
| 2006/0074292 A1* | 4/2006 | Thomson | A61B 6/032 600/411 |
| 2015/0265368 A1* | 9/2015 | Chopra | A61B 5/062 600/424 |
| 2016/0012592 A1* | 1/2016 | Chou | G06T 7/0034 382/131 |
| 2017/0043184 A1* | 2/2017 | Mori | A61N 5/1049 |
| 2017/0312544 A1* | 11/2017 | Mori | A61N 5/1037 |
| 2017/0319165 A1* | 11/2017 | Averbuch | G06T 7/33 |

* cited by examiner $$G(x_1, \ldots x_N) = \lambda \sum_{i=1}^{N} l_i(x_i) + \sum_{i=1}^{N} d(x_{i+1}, x_i) \quad (1)$$

$$d(x_{i+1}, x_i) = \frac{1}{2\pi\sigma_1} \exp\left(-\frac{\|x_i - x_{i+1}\|^2}{2\sigma_1^2}\right) \quad (2)$$

$$X^l = \{x_1^l, x_2^l, \cdots, x_N^l\} \qquad \text{for } l=1 \text{ to L} \quad (3)$$

$$Y^l = \{y_1^l, y_2^l, \cdots, y_N^l\} \qquad \text{for } l=1 \text{ to L} \quad (4)$$

$$r = \frac{\sum_{j=1}^{N}(m_j - \bar{m})(u_j - \bar{u})}{\sqrt{\sum_{j=1}^{N}(m_j - \bar{m})}\sqrt{\sum_{j=1}^{N}(u_j - \bar{u})}} \quad (5)$$

$$\mathbf{S}_i = A x_i + \mathbf{b} \quad (6)$$

$$\mathbf{S}_i = A_1 x_{1,i} + A_2 x_{2,i} + \mathbf{b} \quad (7)$$

$$\mathbf{S}_i = \sum_{k=1}^{K} A_k x_i^k + \mathbf{b} \quad (8)$$

$$\mathbf{T}_i = A y_i + \mathbf{b} \quad (9)$$

$$\mathbf{T}_i = A_1 y_{1,i} + A_2 y_{2,i} + \mathbf{b} \quad (10)$$

$$\mathbf{T}_i = \sum_{k=1}^{K} A_k y_i^k + \mathbf{b} \quad (11)$$

FIG. 2

$$e = \sum_{m=1}^{M} \|y_{m,s} - y_{m,d}\|_2 \quad (12)$$

$$\bar{X} = \{\bar{x}_1, \cdots, \bar{x}_N\} \quad (13)$$

$$\bar{Y} = \{\bar{y}_1, \cdots, \bar{y}_M\} \quad (14)$$

$$\tilde{x}_{i+1} = x_i + \bar{x}_{i+1} - \bar{x}_i \quad (15)$$

$$G(x_1, \ldots x_N) = \lambda \sum_{i=1}^{N} l_i(x_i) + \sum_{i=1}^{N} d(x_{i+1}, \tilde{x}_{i+1}) \quad (16)$$

$$\bar{r}^l = \bar{r}_1^{\ l} \bar{r}_2^{\ l} \quad (17)$$

$$\bar{X}^p = \{\bar{x}_1^p, \cdots, \bar{x}_N^p\} \quad (18)$$

$$p_s = \arg\max_{p=1,\ldots,P} r_p \quad (19)$$

FIG. 7

MEDICAL IMAGE PROCESSING APPARATUS AND METHOD, AND RADIOTHERAPEUTIC APPARATUS

CROSS-REFERENCE TO RELATED APPLICATIONS

This application is based upon and claims the benefit of priority from Japanese Patent application No. 2016-027432, filed on Feb. 16, 2016, the entire contents of each of which are incorporated herein by reference.

BACKGROUND OF THE INVENTION

Field of the Invention

Embodiments of the present invention relate to a medical image processing technique and a radiotherapeutic technique that irradiate, with a beam, a focus being displaced by a patient's respiration and the like for practicing therapy.

Description of the Related Art

Radiotherapy is a therapeutic technique that irradiates a focus (cancer and the like) of a patient with a therapeutic beam and destroys the focus. Thus, unless irradiation with the therapeutic beam is correctly performed in registration with the position of the focus, there is a possibility that even normal tissue will be destroyed. To address this possibility, therapeutic planning is performed before a therapeutic operation of irradiating the patient with the therapeutic beam.

According to the therapeutic plan, the inside of the patient is CT-imaged, voxel data is obtained, and the position of the focus is three-dimensionally grasped, while the irradiation direction and irradiation intensity of the therapeutic beam are determined so as to achieve a small amount of irradiation onto normal tissue. Furthermore, in a case where the focus resides in a viscus (lungs or the like) being periodically displaced in synchronization with respiration and the like, the irradiation target and timing of the therapeutic beam toward the inside of the patient are examined.

In a stage of the therapeutic operation, the patient is fixed onto a bed at a radiotherapeutic apparatus, and the bed is moved so as to aim the beam from a beam irradiation port at the irradiation target examined in the therapeutic planning. The therapeutic beam is emitted from the beam irradiation port at a timing when the beam aim coincides with the focus being displaced in synchronization with respiration.

It is confirmed whether the beam aim coincides with the focus, by checking an X-ray fluoroscopic image taken though real-time imaging the patient on the bed using an X-ray imager permanently provided for the radiotherapeutic apparatus against a DRR (Digitally Reconstructed Radiograph) reconstructed from the voxel data used in the therapeutic planning into a two-dimensional image.

Unfortunately, X-rays output from the X-ray imager of the radiotherapeutic apparatus has a reduced intensity in order to attenuate the patient's exposure to radiation. Consequently, the focuses imaged in X-ray fluoroscopic images are often unclear. It is difficult to track the displacements of the focuses correctly.

Conventionally, methods are taken to address such cases. One of the methods implants a marker made of gold or the like in vicinity of the focus, and tracks the motion of the marker through the X-ray imager. Another method measures the motion of a body surface using a laser range finder. These methods then compensate the result of tracking the focus displacement.

CITATION LIST

Patent Document: Japanese Patent No. 5610441

Unfortunately, the method of implanting the marker in vicinity of the focus is accompanied by a surgical operation, which causes a problem in that the burden on the patient is heavy.

The method of measuring the motion of the body surface also has a problem in that the relationship between motion information about the body surface and the position of the focus is unstable because the depth of respiration varies according to the state of the patient, and the reliability is low accordingly.

SUMMARY OF THE INVENTION

The embodiments of the present invention are implemented in view of such situations, and have an object to provide a medical image processing technique and a radiotherapeutic technique that can correctly track the focus displacement even in an unclear image on the basis of the correlation with displacement of an internal body portion clearly imaged in a fluoroscopic image.

BRIEF DESCRIPTION OF THE DRAWINGS

FIG. 2 shows definition expressions representing element functions of the medical image processing apparatus according to each embodiment;

FIG. 7 shows definition expressions representing element functions of the medical image processing apparatus according to each embodiment.

DETAILED DESCRIPTION OF THE PREFERRED EMBODIMENTS

First Embodiment

Embodiments of the present invention are hereinafter described with reference to the accompanying drawings.

Figure 1:
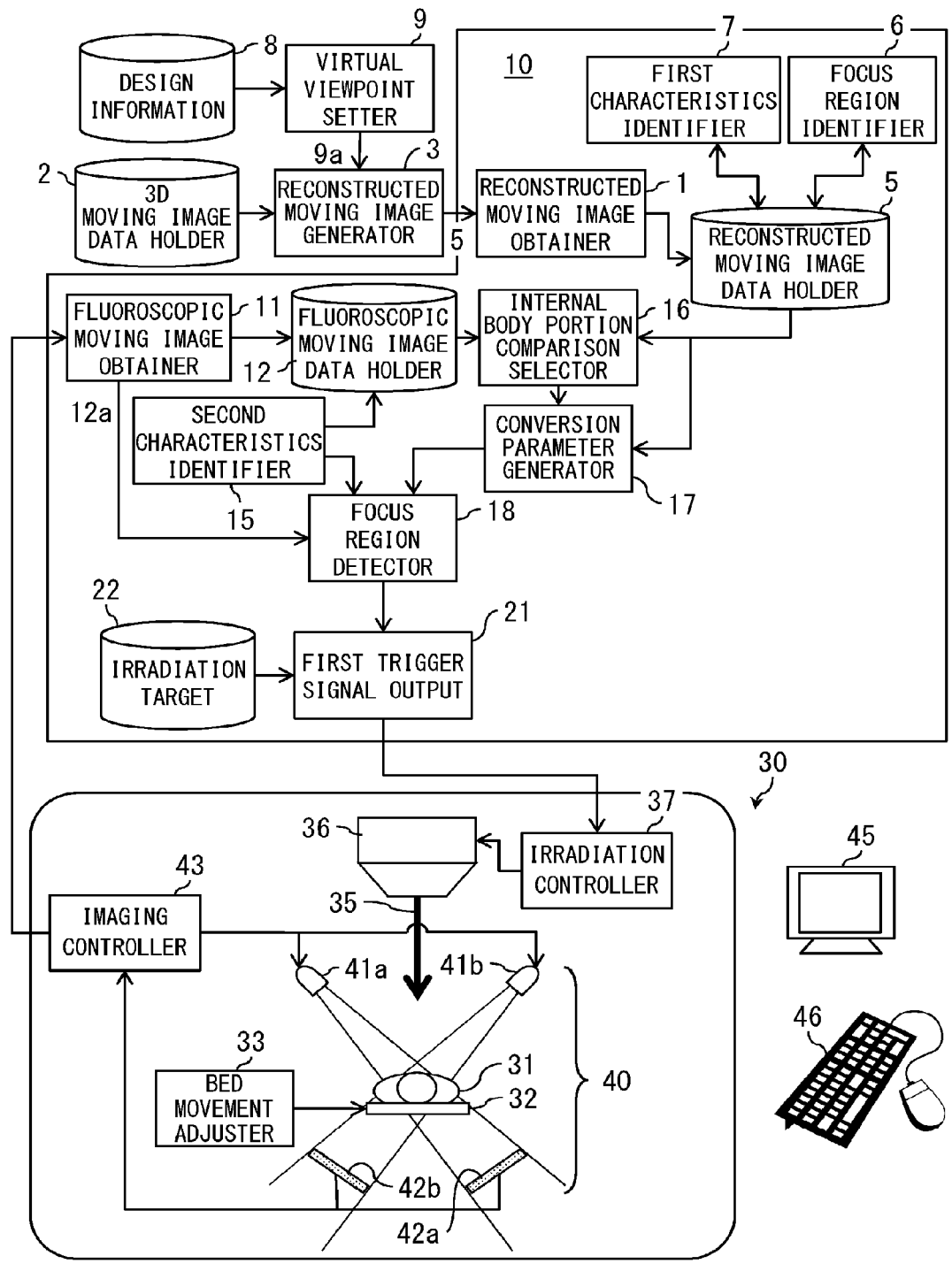
FIG. 1 is a block diagram showing a radiotherapeutic apparatus and a medical image processing apparatus according to a first embodiment of the present invention.

As shown in FIG. 1, the medical image processing apparatus 10 according to the first embodiment comprises: a reconstructed moving image obtainer 1 that obtains a reconstructed moving image 5 where at least one-period data of a three-dimensional moving image 2 is reconstructed on a virtual plane from a set virtual viewpoint 9a, the three-dimensional moving image being obtained by a medical three-dimensional imager (not shown) which images the inside of a patient (not shown) with designation of a region of a focus being displaced in synchronization with respiration; a focus region identifier 6 that identifies a first focus region corresponding to the designated focus, in the reconstructed moving image 5; a first characteristics identifier 7 that identifies, in the reconstructed moving image 5, two or more first characteristic regions defined by the contours of internal body portions being displaced in synchronization with the respiration; a fluoroscopic moving image obtainer 11 that obtains at least one-period data of a fluoroscopic moving image 12 (see FIG. 5) obtained by a medical fluoroscopic imager 40 which fluoroscopically images the patient 31 in conformity with the reconstructed moving image 5; a second characteristics identifier 15 that identifies, in the fluoroscopic moving image 12, each of the two or more second characteristics regions corresponding to the internal body portions; a comparison selector 16 that compares the two or more first characteristic regions identified in the reconstructed moving image 5 and the two or more second characteristics regions identified in the fluoroscopic moving image 12 with respect to combinations having the coinciding internal body portion, and selects any one of the internal body portions where correlation of displacement is achieved; a conversion parameter calculation unit 17 that calculates a conversion parameter for converting the first characteristic region corresponding to the selected internal body portion into the first focus region being displaced in the same phase in the reconstructed moving image 5; and a focus region detector 18 that detects the second focus region being displaced in the fluoroscopic moving image 12, based on the conversion parameter and the second characteristics region corresponding to the selected internal body portion.

Such a configuration of the medical image processing apparatus 10 can correctly track the focus that repeats periodic displacement in synchronization with respiration in an X-ray fluoroscopic moving image 12 where the focus is unclearly rendered; this unclarity is due to attenuation of irradiation intensity for the sake of reduction in exposure of the patient 31 to radiation.

That is, the reconstructed moving image 5 is generated where a focus three-dimensionally designated from the three-dimensional moving image 2 preliminarily taken by a medical three-dimensional imager is reconstructed on a virtual plane. The first characteristic regions in internal body portions (diaphragm etc.) being displaced in synchronization with the respiration are identified in the reconstructed moving image 5. Only one of the internal body portions is to be finally selected. However, multiple body portions are selected at this time.

Next, the second characteristics region in the fluoroscopic moving image 12 is compared with the corresponding first characteristic region in the reconstructed moving image 5. An internal body portion where the loci of displacements of the first characteristic region and the second characteristics region most coincide with each other is selected. It is herein assumed that the second characteristics region is clearly rendered in the fluoroscopic moving image 12.

When the correlation of motions of the reconstructed focus region and the first characteristic region in the reconstructed moving image 5 coincides with the correlation of motions of the unclear focus region and the clear second characteristics region in the fluoroscopic moving image 12 and furthermore the correlation of motions of the first characteristic region and the second characteristics region coincides, the position of the focus that is unclear in the fluoroscopic moving image 12 can be correctly identified.

That is, a calculation process of the second characteristics region in the fluoroscopic moving image 12 through use of the conversion parameter calculated from the positional relationship between the focus region and the first characteristic region in the reconstructed moving image 5 can correctly identify the unclear focus region in the fluoroscopic moving image 12.

The medical image processing apparatus 10 according to the first embodiment further includes a renderer (not shown), and the first trigger signal output 21. The renderer renders the second focus region in the fluoroscopic moving image 12. The first trigger signal output 21 outputs the first trigger signal at a timing when the second focus region rendered in the fluoroscopic moving image 12a transmitted in real time from the medical fluoroscopic imager 40 is displaced to the designated irradiation target 22.

Such a configuration of the medical image processing apparatus 10 can correctly detect the focus that repeats periodic displacement in synchronization with respiration and is unclearly rendered, from the real-time X-ray fluoroscopic moving image 12 of the patient 31, and track the focus in real time. Consequently, the timing when the focus is irradiated with the therapeutic beam 35 can be correctly grasped.

As shown in FIG. 1, a radiotherapeutic apparatus 30 comprises: a bed movement adjuster 33 that moves a bed 32 onto which a patient 31 is fixed, and adjusts a beam aim of a beam irradiation port 36 so as to coincide with an irradiation target 22 preliminarily designated on the locus of the focus being displaced; an imaging controller 43 that controls the medical fluoroscopic imager 40 that generates the fluoroscopic moving image 12a in which the patient 31 is fluoroscopically captured, and transmits the fluoroscopic moving image 12a to the fluoroscopic moving image obtainer 11 of the medical image processing apparatus 10; and an irradiation controller 37 that performs irradiation with a therapeutic beam 35 from the beam irradiation port 36 at a timing of receiving the trigger signal output from the medical image processing apparatus 10.

Here, the therapeutic beam 35 is radiations with which focal tissue, such as of cancer, is irradiated to kill the cells. Such radiations may include X-rays, γ-rays, electron beams, proton beams, neutron beams, and heavy particle beams.

The radiation dose to normal tissue around the focus can be reduced to the minimum by irradiating the focal tissue with the therapeutic beam 35 in multiple directions while turning the beam irradiation port 36 about the anteroposterior axis of the patient 31 and changing the position of the patient 31.

The therapeutic planning is performed at another site before a therapeutic operation of irradiating the patient 31 with the therapeutic beam 35 by the radiotherapeutic apparatus 30. According to the therapeutic plan, a three-dimensional moving image of the inside of the patient is taken by the medical three-dimensional imager. The image is taken with the attitude of the patient being the same as the attitude where the patient is to be fixed to the bed 32 and irradiated with the therapeutic beam 35 in the subsequent therapeutic operation.

The medical three-dimensional imager applied to this embodiment may be an imager of X-ray CT (Computed Tomography), MRI (magnetic resonance imaging) or the like, and can obtain a three-dimensional image (voxel data) of the inside of the patient's body including the focus. Furthermore, the medical three-dimensional imager can take a three-dimensional moving image where temporal variation in respiratory period is captured.

According to the therapeutic plan, the irradiation target 22 in the patient's body is examined. At this target, the focus being displaced in synchronization with respiration or the like is irradiated with the therapeutic beam. Further, the setting position of the bed 32 of the radiotherapeutic apparatus 30 is determined so that the aim of the therapeutic beam 35 can coincide with the irradiation target 22. Furthermore, according to the therapeutic plan, the radiation dose, the irradiation angle, the irradiation range, and the number of irradiation times of therapeutic beams 35 with which the focus is to be irradiated are determined.

The three-dimensional moving image 2 where the inside of the breathing patient is captured for at least one period is stored in a data storage in a state where a region of the focus being displaced in synchronization with respiration is designated by a doctor. The data format of the stored three-dimensional moving image 2 is not specifically limited. It is assumed that in a case where still images at different respiratory phases are captured, the designated region of the focus and the characteristic region are clearly rendered to an extent allowing the region to be discriminated from other organs.

Design information 8 is design information that indicates the mechanical positions, angles and the like of X-ray generators 41 (41a and 41b) and X-ray image receivers 42 (42a and 42b) in a spatial coordinate system; the X-ray generators constitute the medical fluoroscopic imager 40.

The reconstructed moving image generator 3 sets the X-ray generator 41 at the virtual viewpoint 9a on the basis of the design information 8, and generates the reconstructed moving image 5 where the three-dimensional moving image 2 taken by imaging the patient is reconstructed on the virtual plane virtually placed on the X-ray image receiver 42.

The reconstructed moving image 5 is a DRR (Digitally Reconstructed Radiograph) where the three-dimensional moving image 2 is reconstructed into a plane. This image 5 is generated as an aggregate of brightness values on pixels obtained by totalizing the voxel brightness values of the three-dimensional moving image 2 residing along lines connecting the pixels constituting the virtual plane and the virtual viewpoint 9a; the totalization is made along the lines. The generated reconstructed moving image 5 is passed through the obtainer 1 and is held in a data holder of the medical image processing apparatus 10.

The reconstructed moving image 5 held in the data holder may be made up of a file format for a moving image. Alternatively, this image 5 may be made up of multiple still images at different respiratory phases.

The focus region identifier 6 identifies the first focus region corresponding to the focus designated in the three-dimensional moving image 2, from the reconstructed moving image 5 in the data holder. More specifically, what is reconstructed on the virtual plane from the virtual viewpoint 9a on the basis of the region of the focus three-dimensionally identified in the three-dimensional moving image 2 is identified as the first focus region.

Likewise, the first characteristics identifier 7 identifies at least two first characteristic regions defined by the contour of the internal body portion being displaced in synchronization with respiration, from the reconstructed moving image 5 displayed on a monitor 45.

The internal body portions adopted as the first characteristic regions may be a diaphragm, a part of lungs, a part of a liver, a costa and the like. The portions are not specifically limited only if the portions are repeatedly displaced in synchronization with respiration.

The first characteristic region may be designated by a manual operation by an operator. Alternatively, the region may be designated by an automatic function, for example, edge detection, contour detection, template matching or the like.

An example of a processing method of defining the contour of the internal body portion is described, the method being performed on the still image extracted from the reconstructed moving image 5 in the first characteristics identifier 7. The processing method is equally applied also to the second characteristics identifier 15, described later.

The characteristic region can be designated by automatically detecting boundaries at boundary positions having a high contrast in the image, such as the boundaries of a diaphragm or a lung field, through image processing. The boundary detecting method may be an ACM (Active Contour Model), a Level Set method or the like. After the boundaries are detected from the image, one point is selected from among anatomically identical positions. For example, a point on the boundary having the highest absolute value of difference between pixels across the boundary is selected. For example, the first characteristic region automatically detects the boundary position having a high contrast in a predetermined region in the image through the image processing.

Here, the predetermined region is a ling segment input onto an image by the operator. It is preferable that the predetermined region should be positioned on the boundary in a region imaged to have a high contrast in the image, such as the boundary of the diaphragm or lung field. The number of predetermined regions is at least one.

The positions of the characteristic regions included in N images at different respiratory phases are represented as $X=\{x_1, \ldots, x_N\}$. Here, $x_i$ is a two-dimensional vector that represents the characteristic region in the i-th image. That is, $x_1, \ldots, x_N$ represent the locus of the characteristic region from the first to N-th images. An objective function $G(x_1, \ldots, x_N)$ pertaining to the locus of the characteristic region is defined as Expression (1) in FIG. 2.

Here, $li(x_i)$ is a likelihood function that represents the likelihood of the characteristic region at the pixel position $x_i$ in the i-th image. $d(x_{i+1}, x_i)$ is a function that pertains to the positions of the i-th and (i+1)-th characteristic regions, and represents a model of motion. $\lambda$ is a constant value, and is set by the operator.

For example, in a case where the boundary or the like of the diaphragm or lung field is adopted as the characteristic region, the likelihood function outputs a convolution value by a Sobel operator for obtaining the edge intensity of the image. Alternatively, a convolution value by a Laplacian operator is output. Alternatively, a convolution value by an edge detection operator, such as a Canny operator, in image processing is output. Alternatively, the difference value between the pixel values of sequential two images is output. Alternatively, the product of at least two output values among these values is output.

For example, an image in a predetermined region is prepared as a template image, and the similarity with the template image centered at $x_i$ may be output as the likelihood function. The similarity may be, for example, a cross-correlation value, a normalized cross-correlation, a mutual information amount or the like.

The model of motion is represented by Expression (2) in FIG. 2, for example.

To obtain efficiently the loci $x_1, \ldots, x_N$ of the characteristic regions that maximizes the objective function $G(x_1, \ldots, x_N)$, an optimization scheme, for example, a dynamic programming method, may be used.

In a case of multiple predetermined regions, the locus of the characteristic region is obtained by a method similar to that described above, for each region. In a case of L predetermined regions, the locus of each first characteristic region is represented by Expression (3) in FIG. 2, and the locus of each second characteristic region is represented by Expression (4) in FIG. 2.

Function configuration elements assigned symbols 1 to 9 in the medical image processing apparatus 10 perform processes in the therapeutic planning stage, after the three-dimensional moving image 2 is obtained by X-ray CT or the like.

Figure 4:
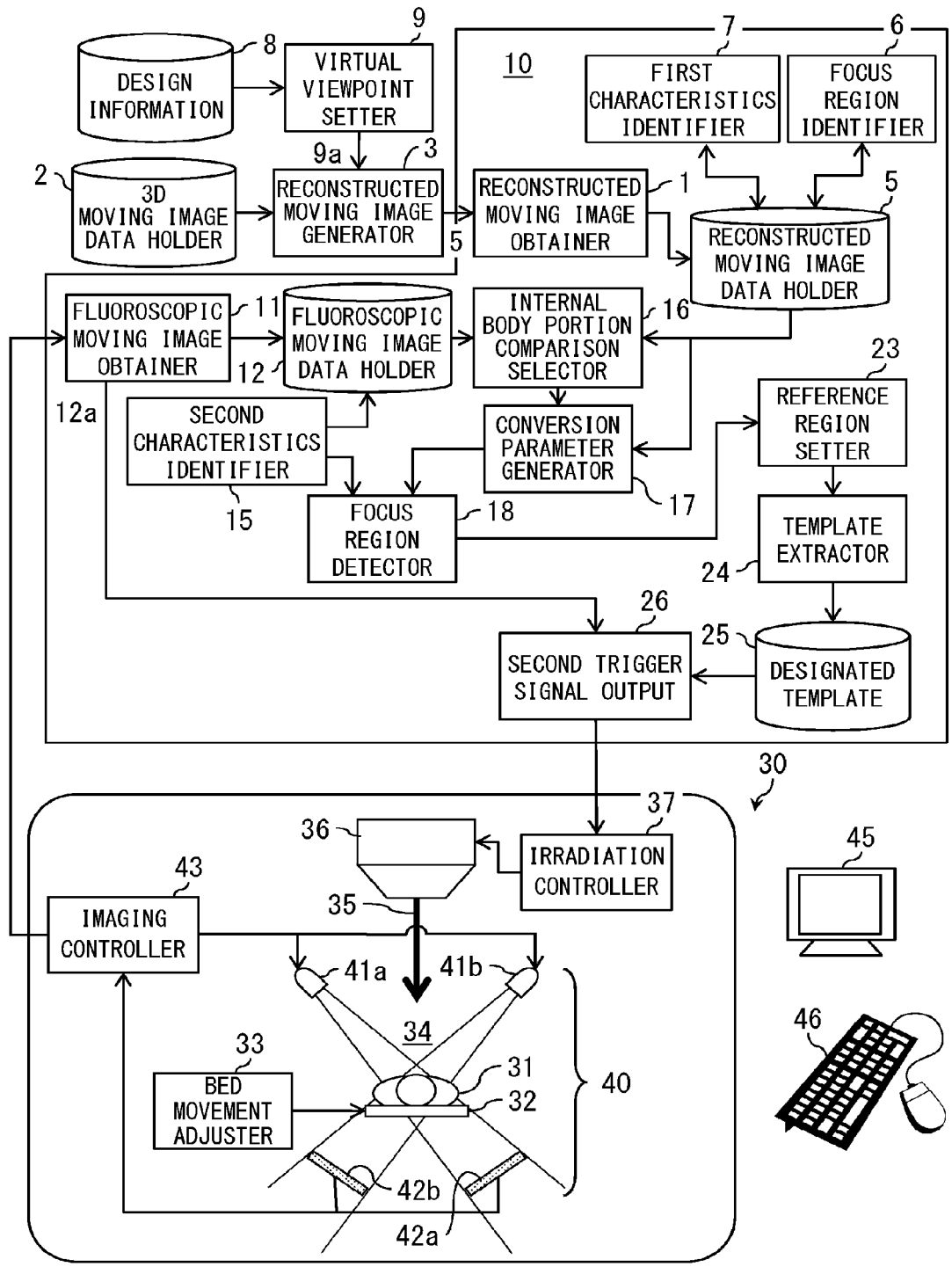
FIG. 4 is a block diagram showing a radiotherapeutic apparatus and a medical image processing apparatus according to a second embodiment.
Figure 6:
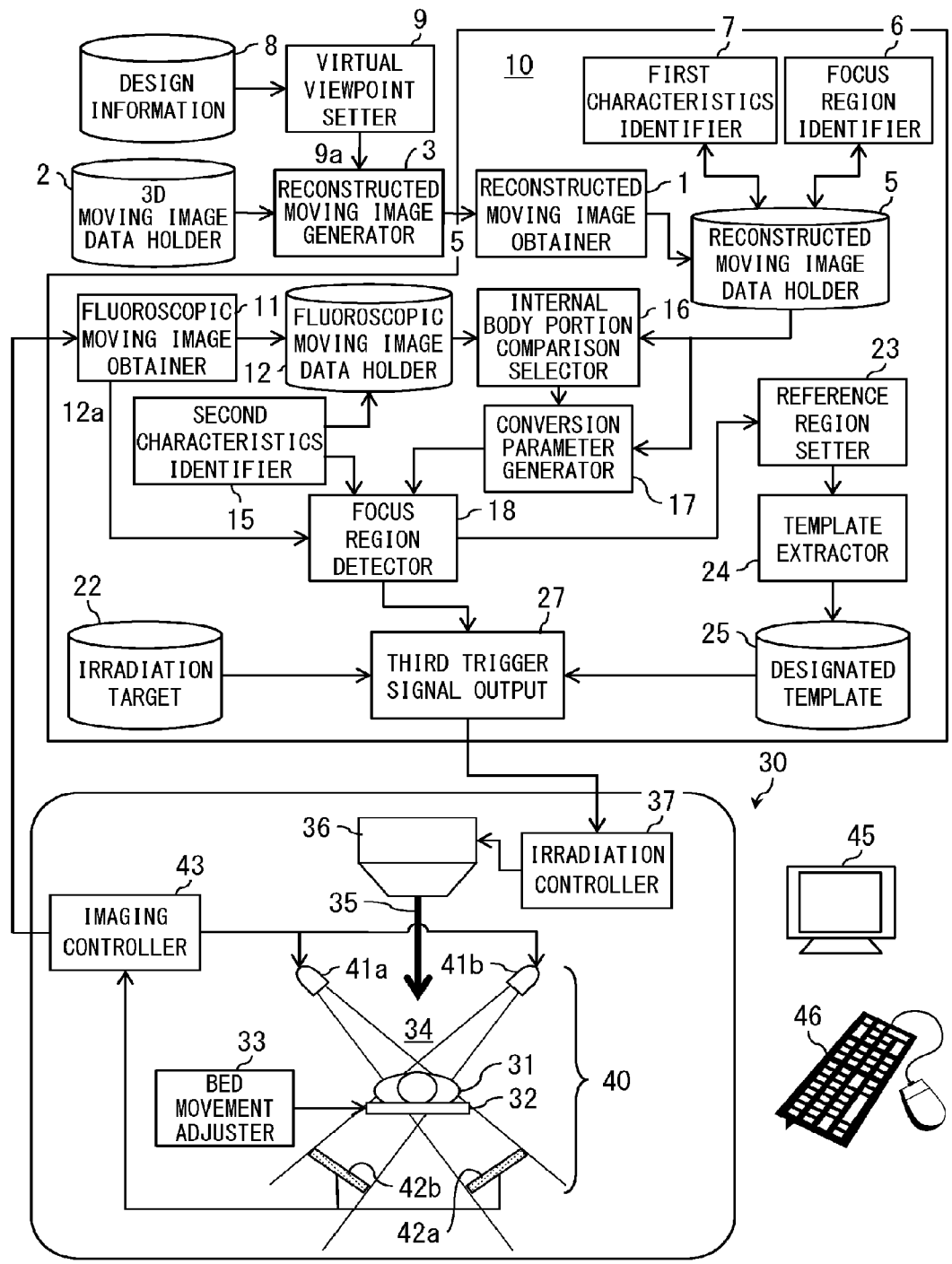
FIG. 6 is a block diagram showing a radiotherapeutic apparatus and a medical image processing apparatus according to a third embodiment.

Function configuration elements assigned symbols 11 to 27 in the medical image processing apparatus 10 in FIGS. 1, 4 and 6 perform processes in the therapeutic operation stage, after the patient 31 is set at the beam aim of the radiotherapeutic apparatus 30.

Before description of the function configuration elements (symbols 11 to 27) of the medical image processing apparatus 10 that execute the processes in the therapeutic operation stage, the radiotherapeutic apparatus 30 is herein described.

The radiotherapeutic apparatus 30 includes the beam irradiation port 36, the irradiation controller 37, the bed 32, the bed movement adjuster 33, the medical fluoroscopic imager 40, and the imaging controller 43. The beam irradiation port 36 emits the therapeutic beam 35 for irradiation. The irradiation controller 37 receives the trigger signal, and controls the irradiation timing of the therapeutic beam 35. The patient 31 is fixed onto the bed 32. The bed movement adjuster 33 aims the therapeutic beam 35 at the position of the focus of the patient 31. The medical fluoroscopic imager 40 takes the fluoroscopic moving image 12 of the patient 31 after aiming. The imaging controller 43 controls the medical fluoroscopic imager 40, and transmits the taken fluoroscopic moving image 12 of the patient 31 to the obtainer 11 of the medical image processing apparatus 10.

The medical fluoroscopic imager 40 includes the pair of X-ray generators 41 (41a and 41b) and the pair of X-ray image receivers 42 (42a and 42b). The X-ray image receiver 42 includes X-ray detection elements arranged in a two-dimensional array, and forms the fluoroscopic moving image 12 according to the amount of attenuation of energy of X-rays that have been emitted from the X-ray generator 41, passed through the patient 31 and reached the detection elements.

The bed movement adjuster 33 moves the bed 32, onto which the patient 31 is fixed, to adjust the beam aim of the beam irradiation port 36 so as to coincide with the irradiation target 22 preliminarily designated on the locus of the focus being displaced. The irradiation target 22 has already been determined in the therapeutic planning stage described above.

The imaging controller 43 instructs the X-ray generators 41 to start irradiation. During irradiation with the X-rays, the X-rays having passed through the patient 31 are detected by the X-ray image receivers 42, and the formed fluoroscopic moving image 12a is transmitted to the fluoroscopic moving image obtainer 11.

It is herein described that the therapeutic operation step after setting of the patient 31 at the radiotherapeutic apparatus 30 can be divided into an off-line period and an on-line period. The off-line period is a period for selecting the internal body portion that is most suitable to identify the focus region from among several internal body portion in the fluoroscopic moving image 12. The on-line period is a period for detecting the focus region from the fluoroscopic moving image 12 transmitted in real time using the internal body portion selected in the off-line period and performing irradiation with the therapeutic beam 35.

In the off-line period, the fluoroscopic moving image obtainer 11 receives the fluoroscopic moving image 12 transmitted from the medical fluoroscopic imager 40, and stores this image in the data holder. The fluoroscopic moving image 12 held in the data holder is required to be at least that in one period of respiration.

In the on-line period, the fluoroscopic moving image obtainer 11 transmits the fluoroscopic moving image 12a transmitted from the medical fluoroscopic imager 40 to the focus region detector 18, and causes this detector to detect the focus region in real time.

In the off-line period, the second characteristics identifier 15 identifies at least two internal body portions, as the second characteristics regions, in the fluoroscopic moving image 12 held in the data holder.

In the off-line period, multiple still images where the second characteristics regions with different phases are rendered are extracted from the fluoroscopic moving image 12, the still images are displayed on the monitor 45, and the second characteristics regions are identified through the input unit 46. More specifically, the second characteristics region can be identified according to a method analogous to the method having already described in the first characteristics identifier 7 (Expression (4) in FIG. 2). The identification method is not specifically limited.

In the on-line period, the second characteristics identifier 15 identifies at least two internal body portions, as the second characteristics regions, in the fluoroscopic moving image 12a transmitted in real time from the medical fluoroscopic imager 40. In the on-line period, the manual operation cannot be applied, and the second characteristics regions are identified by the automatic function instead.

The comparison selector 16 compares two or more first characteristic regions identified in the reconstructed moving image 5 in the data holder and two or more second characteristics regions identified from the fluoroscopic moving image 12 in the data holder with respect to combinations having the coinciding internal body portions, and selects any one internal body portion where correlation of displacement is achieved.

Next, an example of the method of determining the correlation between the first characteristic region and the second characteristics region through the comparison selector 16 is described.

Provided that $x_i = (m_i, n_i)$, $y_i = (u_i, v_i)$ in Expressions (1) to (4) in FIG. 2, the correlation coefficient r pertaining to the x-coordinate is obtained according to Expression (5) in FIG. 2. Likewise, the correlation coefficient pertaining to the y-coordinate indicated by the locus may be obtained. Alternatively, the product of these values may be adopted as the correlation.

The description has been made assuming that the time interval for sampling the still image from the reconstructed moving image 5 is the same as the time interval for sampling the still image from the fluoroscopic moving image 12. If the time intervals are different from each other, the time intervals and the phases are required to be aligned by an appropriate extrapolation process.

In a case where multiple (L) internal body portions are selected, the correlation of combination between the first characteristic region and the second characteristics region is obtained by the method described above. The internal body portion having the most excellent value is selected as the internal body portion that is subsequently used to generate the conversion parameter. Alternatively, a threshold may be set for the correlation value and used as a reference for selection.

The conversion parameter calculation unit 17 calculates the conversion parameter for converting the first characteristic region corresponding to the internal body portion selected by the comparison selector 16 into the first focus region being displaced in the same phase in the reconstructed moving image 5.

Next, an example of a method of calculating the conversion parameters in the conversion parameter calculation unit 17 is described. The conversion parameter is obtained by applying a calculation process to the locus $X=\{x_1, \ldots, x_N\}$ of the first characteristic region and the locus $S=\{S_1, \ldots, S_N\}$ of the focus region.

The positional relationship between the first characteristic region and the focus region is represented by Expression (6) in FIG. 2, which is a regression equation. Here, A is a 2×3 matrix, and b is a three-dimensional column vector. In this case, the conversion parameters to be obtained are A and b. These conversion parameters are obtained by the least squares method.

Next, a case is discussed where the fluoroscopic moving image 12 is taken in two directions as represented in the medical fluoroscopic imager 40 in FIG. 1. In this case, the locus of the first characteristic region obtained from the reconstructed moving image 5 generated from the virtual viewpoint corresponding to the direction 1 is a locus $X_1=\{x_{1,1}, \ldots, x_{1,N}\}$, and the locus of the first characteristic region obtained from the reconstructed moving image 5 generated from the virtual viewpoint corresponding to the direction 2 is the locus $X_2=\{x_{2,1}, \ldots, x_{2,N}\}$. The positional relationship between the first characteristic region and the focus region is thus represented by Expression (7) in FIG. 2, which is a regression equation. Here, $A_1$ and $A_2$ are 2×3 matrices, and b is a three-dimensional column vector. In this case, the conversion parameters to be obtained are $A_1$, $A_2$ and b. These conversion parameters are obtained by the least squares method.

Next, in a case of K first characteristic regions, the positional relationship between the first characteristic region and the focus region is thus represented by Expression (8) in FIG. 2, which is a regression equation. Here, $A_k$ is a 2×3 matrix, and b is a three-dimensional column vector. In this case, the conversion parameters to be obtained are $A_k$ and b. These conversion parameters are obtained by the least squares method.

The focus region detector 18 detects the second focus region being displaced in the fluoroscopic moving image 12, on the basis of the conversion parameters and the second characteristics region corresponding to the selected internal body portion.

Next, a method of data conversion from the locus of the second characteristics region into the locus of the second focus region in the focus region detector 18.

The locus $T=\{T_1, \ldots, T_N\}$ of the second focus region in the fluoroscopic moving image 12a can be obtained by Expression (9) in FIG. 2 using the locus $Y=\{y_1, \ldots, y_N\}$ of the second characteristics region B and the conversion parameters A and b obtained in the conversion parameter calculation unit 17.

The locus $T=\{T_1, \ldots, T_N\}$ of the second focus region in the fluoroscopic moving image 12a can be obtained by Expression (10) in FIG. 2 using the locus $Y=\{y_1, \ldots, y_N\}$ of the second characteristics region B and the conversion parameters $A_1$, $A_2$ and b obtained in the conversion parameter calculation unit 17.

The locus $T=\{T_1, \ldots, T_N\}$ of the second focus region in the fluoroscopic moving image 12a can be obtained by Expression (11) in FIG. 2 using the locus $Y=\{y_1, \ldots, y_N\}$ of the second characteristics region B and the conversion parameters $A_1, \ldots, A_K$ and b obtained in the conversion parameter calculation unit 17.

The locus of the second focus region is displayed on the monitor 45 on the basis of the fluoroscopic moving image 12 taken in the off-line period, and it is confirmed that the irradiation target 22 resides on the locus.

The first trigger signal output 21 confirms that the second focus region detected by the focus region detector 18 traces the locus set in the off-line period on the basis of the fluoroscopic moving image 12a transmitted in real time in the on-line period, and outputs the first trigger signal at a timing that coincides with that of the irradiation target 22.

The irradiation controller 37 of the radiotherapeutic apparatus 30 irradiates the focus of the patient 31 with the therapeutic beam 35 from the beam irradiation port 36 at a timing of receiving the trigger signal output from the medical image processing apparatus 10.

Figure 3:
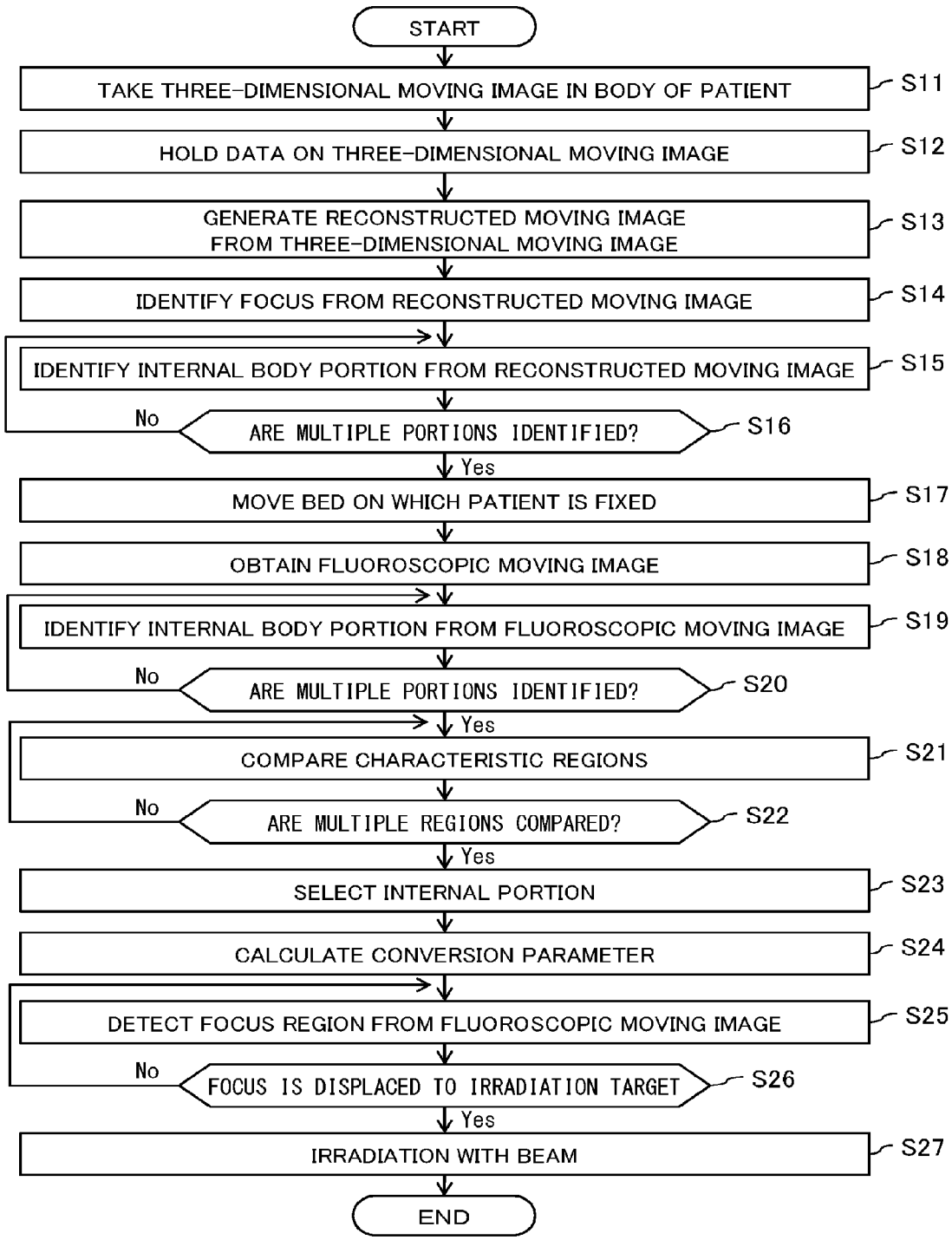
FIG. 3 is a flowchart illustrating operations of a medical image processing method and the radiotherapeutic apparatus according to the first embodiment.

Referring to the flowchart FIG. 3, the operations of a medical image processing method, and the radiotherapeutic apparatus according to each embodiment are described (see FIG. 1 as required).

In the therapeutic planning stage, a three-dimensional moving image that includes the focus in the body of the patient is taken using a medical three-dimensional imager, such as an X-ray CT apparatus (S11). Data on the taken three-dimensional moving image is obtained for at least one respiratory period, the focus region is three-dimensionally designated, and the data is held (S12).

Next, a reconstructed moving image (DDR) is generated that is reconstructed on a virtual plane from the three-dimensional moving image from a virtual viewpoint set from the design information 8 of the medical fluoroscopic imager 40 (S13). The first focus region reconstructed on the plane on the basis of the focus three-dimensionally designated from the reconstructed moving image is identified (S14). From the reconstructed moving image, multiple first characteristic regions defined by the contours of the internal body portions being displaced in synchronized with respiration are identified (S15) (S16).

In the therapeutic planning stage, the displacement position of the focus as the irradiation target 22 of the therapeutic beam 35 is determined.

Next, the processing reaches the off-line steps.

The patient 31 is fixed onto the bed 32, subsequently, the movement and adjustment to the determined position is performed, and the irradiation target 22 in the body of the patient 31 is aligned to the aim of the therapeutic beam 35 (S17). The movement and adjustment of the bed 32 is performed by taking one X-ray fluoroscopic image through the medical fluoroscopic imager 40, comparing the fluoroscopic image with the DDR image, and causing these images to coincide with each other.

The medical fluoroscopic imager 40 is operated to obtain at least one-period data on the fluoroscopic moving image, and the data is held (S18). Each of at least two second characteristics regions corresponding to the internal body portions being displaced in synchronization with respiration from the fluoroscopic moving image is identified (S19) (S20).

At least two first characteristic regions identified in the reconstructed moving image 5 are compared with at least two second characteristics regions identified from the fluoroscopic moving image 12 with respect to the combination with the coinciding internal body portion (S21) (S22). One of the internal body portions that has a displacement orbit being achieved between the reconstructed moving image 5 and the fluoroscopic moving image 12 is selected (S23).

Next, from the relationship in the reconstructed moving image 5 between the focus region and the characteristic region that correspond to the selected internal body portion, a conversion parameter for converting the characteristic region into the focus region is calculated (S24).

Next, the treatment operation reaches the on-line steps.

The characteristic region of the selected internal body portion is identified from the fluoroscopic moving image 12a transmitted in real time from the medical fluoroscopic imager 40, and from the characteristic region the focus region is detected through data conversion based on the conversion parameters (S25).

At a timing when the focus region detected in the fluoroscopic moving image 12a is displaced to the designated irradiation target 22 (S26), the trigger signal is output and the focus of the patient 31 is irradiated with the therapeutic beam 35 (S27) (END).

Second Embodiment

Figure 5:
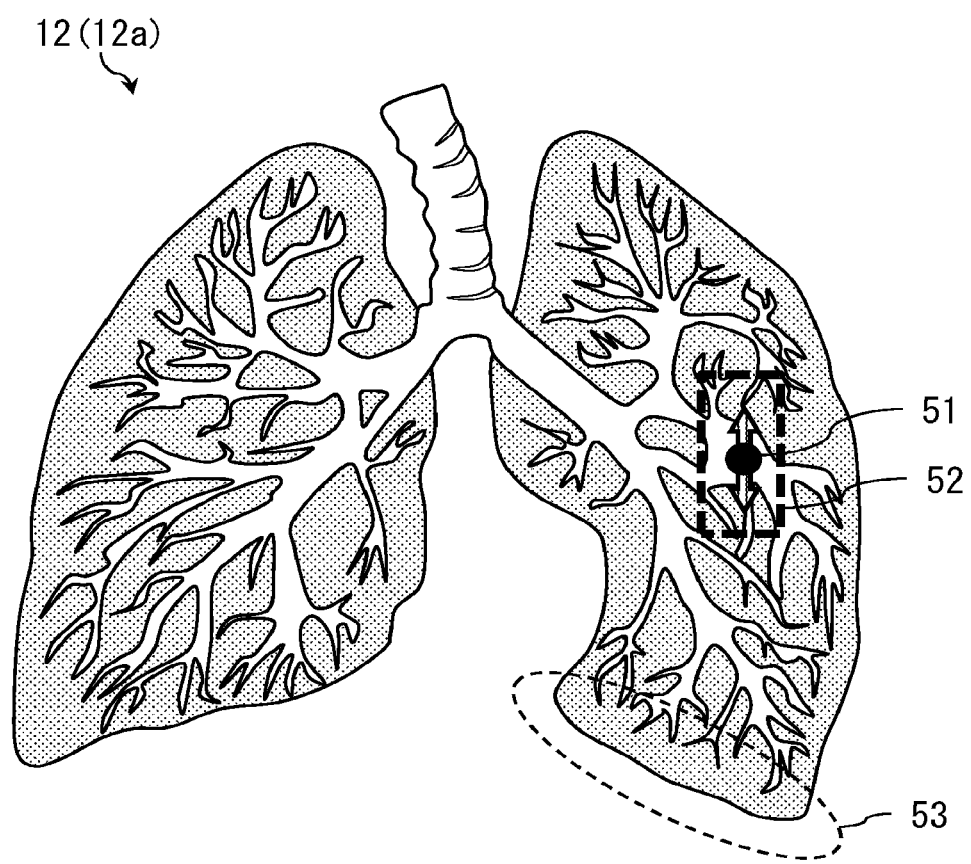
FIG. 5 is a diagram illustrating a reference region applied to the medical image processing apparatus according to the second embodiment.

Next, referring to FIGS. 4 and 5, a second embodiment of the present invention is described. In FIG. 4, elements having configurations or functions common to those in FIG. 1 are assigned the same symbols, and redundant description is omitted.

The medical image processing apparatus 10 according to the second embodiment further comprises: a reference region setter 23 that sets a reference region 52 that includes at least a part of a range where the second focus region 51 (FIG. 5) detected in the fluoroscopic moving image 12 is being displaced in synchronization with the respiration; a template extractor 24 that extracts the reference region 52 that is periodically varying in synchronization with the respiration, as a plurality of templates for different phases; and a second trigger signal output 26 that outputs a second trigger signal at a timing when the reference region 52 periodically varying in synchronization with the respiration in the fluoroscopic moving image 12a transmitted in real time from the medical fluoroscopic imager 40 coincides with any one of the templates 25 that is designated from among the templates.

Such a configuration of the medical image processing apparatus 10 can correctly track, in real time, the focus that repeats periodic displacement in synchronization with respiration and is unclearly rendered, from the real-time X-ray fluoroscopic moving image 12a of the patient 31.

Furthermore, there is no need to identify the second characteristics region 53 in the fluoroscopic moving image 12a in real time, or to detect the second focus region 51 using the conversion parameter. Consequently, calculation delay is eliminated accordingly. Consequently, the timing when the focus is irradiated with the therapeutic beam 35 can be more correctly grasped.

The reference region setter 23 uses information on the second focus region 51 detected by the focus region detector 18, on the basis of the fluoroscopic moving image 12 obtained in the off-line steps of the therapeutic operation (and held in the data holder). A region that includes at least a part of the second focus region 51 being displaced in synchronization with respiration is set in the reference region 52. The image of the reference region 52 varies in synchronization with displacement of respiration.

The template extractor 24 extracts, as templates, multiple images varying according to the respiratory phase in the reference region 52 set in the fluoroscopic moving image 12. The thus extracted templates correspond to the focus displacements at different positions according to the respiratory phases in the fluoroscopic moving image 12. The template extractor 24 designates one template 25 corresponding to the irradiation target in the body of the patient determined in the therapeutic plan from among the thus extracted templates.

The second trigger signal output 26 outputs the second trigger signal at a timing when the image of the reference region 52 of the fluoroscopic moving image 12a transmitted from the medical fluoroscopic imager 40 in real time coincides with the image of the designated template 25.

The irradiation controller 37 of the radiotherapeutic apparatus 30 irradiates the focus of the patient 31 with the therapeutic beam 35 from the beam irradiation port 36 at a timing of receiving the trigger signal output from the medical image processing apparatus 10.

Third Embodiment

Next, referring to FIG. 6, a third embodiment of the present invention is described. In FIG. 6, elements having configurations or functions common to those in FIGS. 1 and 4 are assigned the same symbols, and redundant description is omitted.

The medical image processing apparatus 10 in the third embodiment has a configuration where the first and second embodiments are combined. Furthermore, a third trigger signal output 27 is provided that outputs a third trigger signal at a timing when the focus region detected on the basis of the fluoroscopic moving image 12a transmitted to the detector 18 in real time and the position of the focus recorded in the designated template 25 are in a predetermined range, and the detected focus region is displaced to the irradiation target 22.

In the first embodiment, the position of the focus is detected in the fluoroscopic moving image 12a transmitted from the medical fluoroscopic imager 40 in real time on the basis of the identified internal body portion, and the timing when this position coincides with the beam aim is detected.

On the other hand, in the second embodiment, the timing when the reference region 52 in the fluoroscopic moving image 12a transmitted from the medical fluoroscopic imager 40 in real time coincides in view of image with the designated template is detected.

Due to such a difference of processes, strict coincidence between the timing obtained in the first embodiment and the timing obtained in the second embodiment is not necessarily secured.

To address such insecurity, in the third embodiment, the coincidence between both the timings is instantaneously evaluated. If coincidence is determined, the trigger signal is output to the irradiation controller 37. If no coincidence is determined, no trigger signal is output.

Such determination of presence or absence of coincidence between both the timings is performed by preliminarily recording the position of the focus region in the designated template 25 and by performing threshold determination of the coincidence between the position of the focus region recorded in the template 25 and the position of the focus region detected by the focus region detector 18. Alternatively, threshold determination may be made on the temporal difference in output timing between the first trigger signal output in the first embodiment and the second trigger signal output in the second embodiment.

Consequently, the accuracy of timing when the focus is correctly irradiated with the therapeutic beam 35 can be improved.

Next, an example of a processing method for the sake of improving the accuracy of timing of emitting the therapeutic beam 35 in the third trigger signal output 27 is described.

First, it is assumed that the locus of the focus region recorded in the template 25 is $Y_d=\{y_{1,d}, \ldots, y_{M,d}\}$, and the locus of the focus region detected by the focus region detector 18 is $Y_s=\{y_{1,s}, \ldots, y_{M,s}\}$. These $Y_d$ and $Y_s$ are obtained in the off-line period.

The coincidence e between both the values is defined as in Expression (12) in FIG. 7. When the coincidence is in a predetermined range, the processing transitions to the on-line period, and the third trigger signal is output at a timing when the detected focus region is displaced to the irradiation target 22.

Here, $\|x\|$ represents the Euclidean norm of a vector x. In a case where the coincidence e has a value in the predetermined threshold, the trigger signal is output. In other cases, no trigger signal is output, real-time obtainment of the fluoroscopic moving image 12a is continued, and the algorithm for determining the irradiation timing is continued.

Other Embodiments of First Characteristics Identifier 7, Second Characteristics Identifier 15, and Comparison Selector 16

A method for further accurately identifying, as characteristic regions, internal body portions included in the reconstructed moving image 5 and the fluoroscopic moving images 12 and 12a is hereinafter described.

In each embodiment, the first characteristics identifier 7 and the second characteristics identifier 15 detect the boundary of the image according to the spatial derivative value of pixel values pertaining to a local portion in the image. Although it is sufficient in a case of high contrast imaging, the radiation dose of X-rays with which the patient 31 is irradiated in the medical fluoroscopic imager 40 is required to be increased in order to improve the image quality of the fluoroscopic moving image 12. The increase may affect the human body.

In order to detect the second characteristics region in the fluoroscopic moving image 12 highly accurately even in a case of a reduced radiation dose in the medical fluoroscopic imager 40, more robust detection of the characteristic region through use of image information ranging widely around the second characteristics region is discussed.

The first characteristics identifier 7 obtains a first motion vector in the reconstructed moving image (DDR). The second characteristics identifier 15 detects a second motion vector in the fluoroscopic moving image 12.

Here, the motion vector means the motion vector at any position in a predetermined region. More preferably, the motion vector means the barycenter position of the predetermined region. Here, the locus of the first motion vector is defined as in Expression (13) in FIG. 7. The locus of the second motion vector is defined as in Expression (14) in FIG. 7.

There are various methods of obtaining the motion vector of an image. A method of obtaining an optical flow representing the motion vector at a certain point on an image may be the gradient method and the Lucas-Kanade method. Alternatively, an image in a predetermined region may be adopted as a template, and a motion vector in the predetermined region may be obtained by template tracking.

The first characteristic region on time i+1 is predicted using the locus of the first motion vector. The position of the predicted first characteristic region on time i+1 is defined as in Expression (15) in FIG. 7.

Through use of this Expression (15), an objective function $G(x_1, \ldots, x_N)$ pertaining to the locus of the first characteristic region is defined as Expression (16) in FIG. 7. Likewise, an objective function $G(y_1, \ldots, y_N)$ pertaining to the locus of the second characteristics region is defined.

The comparison selector 16 obtains the first characteristic region and the first motion vector from the data storage for the reconstructed moving image 5, and obtains the second characteristics region and the second motion vector from the data storage for the fluoroscopic moving image 12.

The comparison selector 16 compares not only the combination of the first characteristic region and the second characteristics region but also the combination of the first motion vector and the second motion vector, and selects any one of the internal body portions that has the correlation of displacement.

The comparison selector 16 obtains the correlation between the first motion vector and the first characteristic region according to Expression (5) in FIG. 2. The correlation between the first characteristic region and the first motion vector is defined as the first term of the right-hand side of Expression (17) in FIG. 7.

Furthermore, the comparison selector 16 obtains the correlation between the second motion vector and the second characteristic region according to Expression (5) in FIG. 2. The correlation between the first second characteristic region and the second motion vector is defined as the second term of the right-hand side of Expression (17) in FIG. 7. Furthermore, the product of both values is obtained, and the product is defined as the correlation value of Expression (17) in FIG. 7.

In the comparison selector 16, the body portion where the correlation value represented by the left-hand side of Expression (17) in FIG. 7 is the most excellent value is selected as the internal body portion that is subsequently used to generate the conversion parameter. Alternatively, a threshold may be set for the correlation value and used as a reference for selection.

Other Embodiments of First Characteristics Identifier 7, Second Characteristics Identifier 15, and Focus Region Identifier 6

A method of automatically and correctly identifying the characteristic region and the focus region is described.

Motion vectors at P points are obtained, and the obtained locus is defined as Expression (18) in FIG. 7. The locus of the barycenter of a tumor region in different respiratory phases is defined $S=\{S_1, \ldots, S_N\}$.

The correlation $r_p$ between the locus of a certain point p and the locus of the barycenter of the tumor is derived from Expression (5) in FIG. 2. Based on Expression (19) in FIG. 7, a point p having the highest correlation with the locus of the barycenter of the tumor is obtained, and a certain region around the point p including this point is output as an identification region.

The medical image processing apparatus of at least one embodiment described above can select an internal body portion having the most coinciding locus of displacement is selected in the moving image obtained by reconstructing the three-dimensional moving image on a plane and in the fluoroscopic moving image, and correctly detect and track the focus whose rendered image is unclear in the fluoroscopic moving image on the basis of the correlation with the displacement of the selected internal body portion.

Some embodiments of the present invention have been described above. These embodiments have been presented as examples. There is no intention to limit the scope of the invention. These embodiments can also be implemented in other various modes, and variously omitted, replaced, changed, and combined without departing from the gist of the invention. The embodiments and their variations are encompassed by the scope and gist of the invention. Likewise, these embodiments and variations are encompassed by the invention described in the claims and its range of equivalence.

The medical image processing apparatus 10 described above includes: a control device; an external storing device; a display device, such as a display; an input device, such as a mouse and a keyboard; and a communication I/F. In the control device, a processor, such as a dedicated chip, FPGA (Field Programmable Gate Array), GPU (Graphics Processing Unit), or CPU (Central Processing Unit), is highly integrated. The storing device may be ROM (Read Only Memory), RAM (Random Access Memory) or the like. The external storing device may be a HDD (Hard Disk Drive), an SSD (Solid State Drive) or the like. This apparatus can be implemented by a hardware configuration through use of a typical computer.

The program executed in the medical image processing apparatus 10 is preliminarily implemented in an ROM or the like and provided. Alternatively, the program may be stored in a computer-readable storing medium in an installable or executable form. This medium may be a CD-ROM, CD-R, memory card, DVD, flexible disk (FD) or the like.

The program executed in the medical image processing apparatus 10 according to this embodiment may be stored in a computer connected to a network, such as the Internet, downloaded via the network and provided.

The apparatus 10 may be configured by connecting separate modules that independently exert the functions of the configuration elements to each other via the network or a dedicated line, and combining the modules.

What is claimed is:

1. A medical image processing apparatus, comprising:
a reconstructed moving image obtainer;
a focus region identifier;
a first characteristics identifier;
a fluoroscopic moving image obtainer;
a second characteristics identifier;
a comparison selector;
a conversion parameter calculation unit; and
a focus region detector,
wherein the reconstructed moving image obtainer obtains a reconstructed moving image where at least one-period data of a three-dimensional moving image is reconstructed on a virtual plane from a set virtual viewpoint, the three-dimensional moving image being obtained by imaging an inside of a patient with designation of a region of a focus being displaced in synchronization with respiration,
the focus region identifier identifies a first focus region corresponding to the designated focus, in the reconstructed moving image,
the first characteristics identifier identifies, in the reconstructed moving image, two or more first characteristic regions defined by contours of internal body portions being displaced in synchronization with the respiration,
the fluoroscopic moving image obtainer obtains at least one-period data of a fluoroscopic moving image obtained by a medical fluoroscopic imager which fluoroscopically images the patient in conformity with the reconstructed moving image,
the second characteristics identifier identifies, in the fluoroscopic moving image, each of two or more second characteristics regions corresponding to the internal body portions,
the comparison selector compares a locus of displacement of each of the two or more first characteristic regions identified in the reconstructed moving image and a locus of displacement of each of the two or more second characteristics regions identified in the fluoroscopic moving image with respect to combinations having a coinciding internal body portion, and selects any one of the internal body portions where the locus of displacement most coincide with each other,
the conversion parameter calculation unit calculates a conversion parameter for converting the first characteristic region being displaced corresponding to the selected internal body portion into the first focus region being displaced in a same phase in the reconstructed moving image, and
the focus region detector detects a second focus region being displaced in the fluoroscopic moving image, based on the conversion parameter and the second characteristics region being displaced corresponding to the selected internal body portion.

2. The medical image processing apparatus according to claim 1, further comprising:
a renderer; and
a first trigger signal output,
wherein the renderer renders the second focus region in the fluoroscopic moving image, and
the first trigger signal output outputs a first trigger signal at a timing when the second focus region rendered in the fluoroscopic moving image transmitted in real time from the medical fluoroscopic imager is displaced to a designated irradiation target.

3. The medical image processing apparatus according to claim 1, further comprising:
a reference region setter;
a template extractor; and
a second trigger signal output,
wherein the reference region setter sets a reference region that includes at least a part of a range where the second focus region detected in the fluoroscopic moving image is being displaced in synchronization with the respiration,
the template extractor extracts the reference region that is periodically varying in synchronization with the respiration, as a plurality of templates for different phases, and
the second trigger signal output outputs a second trigger signal at a timing when the reference region periodically varying in the fluoroscopic moving image transmitted in real time from the medical fluoroscopic imager coincides with any one of the templates that is designated from among the templates.

4. The medical image processing apparatus according to claim 1, further comprising:
a reference region setter;
a template extractor; and
a third trigger signal output,
wherein the reference region setter sets a reference region that includes at least a part of a range where the second focus region detected in the fluoroscopic moving image is being displaced in synchronization with the respiration, the template extractor extracts the reference region that is periodically varying in synchronization with the respiration, as a plurality of templates for different phases, and the third trigger signal output outputs a third trigger signal at a timing when the focus region detected based on the fluoroscopic moving image transmitted in real time from the focus region detector and a position of the focus recorded in a designated template are in a predetermined range, and the detected focus region is displaced to the irradiation target.

5. A radiotherapeutic apparatus, comprising:
a bed movement adjuster;
an imaging controller; and
an irradiation controller,
wherein the bed movement adjuster moves a bed onto which a patient is fixed, and adjusts a beam aim of a beam irradiation port so as to coincide with an irradiation target preliminarily designated on a locus of the focus being displaced, the imaging controller controls the medical fluoroscopic imager that generates the fluoroscopic moving image in which the patient is fluoroscopically captured, and transmits the fluoroscopic moving image to the fluoroscopic moving image obtainer of the medical image processing apparatus according to claim 2, and the irradiation controller performs irradiation with a therapeutic beam from the beam irradiation port at a timing of receiving the trigger signal output from the medical image processing apparatus according to claim 2.

6. A medical image processing method, comprising:
obtaining a reconstructed moving image where at least one-period data of a three-dimensional moving image is reconstructed on a virtual plane from a set virtual viewpoint, the three-dimensional moving image being obtained by imaging an inside of a patient with designation of a region of a focus being displaced in synchronization with respiration;

identifying a first focus region corresponding to the designated focus, in the reconstructed moving image;

identifying, in the reconstructed moving image, two or more first characteristic regions defined by contours of internal body portions being displaced in synchronization with the respiration;

obtaining at least one-period data of a fluoroscopic moving image obtained by a medical fluoroscopic imager which fluoroscopically images the patient in conformity with the reconstructed moving image;

identifying, in the fluoroscopic moving image, each of the two or more second characteristics regions corresponding to the internal body portions;

comparing a locus of displacement of each of the two or more first characteristic regions identified in the reconstructed moving image and a locus of displacement of each of the two or more second characteristics regions identified in the fluoroscopic moving image with respect to combinations having a coinciding internal body portion, and selecting any one of the internal body portions where the locus of displacement most coincide with each other, calculating a conversion parameter for converting the first characteristic region being displaced corresponding to the selected internal body portion into the first focus region being displaced in a same phase in the reconstructed moving image; and detecting a second focus region being displaced in the fluoroscopic moving image, based on the conversion parameter and the second characteristics region being displaced corresponding to the selected internal body portion.

7. A medical image processing apparatus, comprising:
circuitry configured to
obtain a reconstructed moving image where at least one-period data of a three-dimensional moving image is reconstructed on a virtual plane from a set virtual viewpoint, the three-dimensional moving image being obtained by imaging an inside of a patient with designation of a region of a focus being displaced in synchronization with respiration, identify a first focus region corresponding to the designated focus, in the reconstructed moving image, identify, in the reconstructed moving image, two or more first characteristic regions defined by contours of internal body portions being displaced in synchronization with the respiration, obtain at least one-period data of a fluoroscopic moving image obtained by a medical fluoroscopic imager which fluoroscopically images the patient in conformity with the reconstructed moving image, identify, in the fluoroscopic moving image, each of two or more second characteristics regions corresponding to the internal body portions, compare a locus of displacement of each of the two or more first characteristic regions identified in the reconstructed moving image and a locus of displacement of each of the two or more second characteristics regions identified in the fluoroscopic moving image with respect to combinations having a coinciding internal body portion, and select any one of the internal body portions where the locus of displacement most coincide with each other, calculate a conversion parameter for converting the first characteristic region being displaced corresponding to the selected internal body portion into the first focus region being displaced in a same phase in the reconstructed moving image, and detect a second focus region being displaced in the fluoroscopic moving image, based on the conversion parameter and the second characteristics region being displaced corresponding to the selected internal body portion.

* * * * *